United States Patent
Xiang et al.

(10) Patent No.: US 7,863,977 B1
(45) Date of Patent: Jan. 4, 2011

(54) FULLY DIFFERENTIAL NON-INVERTED PARALLEL AMPLIFIER FOR DETECTING BIOLOGY ELECTRICAL SIGNAL

(75) Inventors: Xiaofei Xiang, Nanshan Shenzhen (CN); Xunqiao Hu, Nanshan Shenzhen (CN); Xicheng Xie, Nanshan Shenzhen (CN)

(73) Assignee: Edan Instruments, Inc. (CN)

( * ) Notice: Subject to any disclaimer, the term of this patent is extended or adjusted under 35 U.S.C. 154(b) by 0 days.

(21) Appl. No.: 12/558,609

(22) Filed: Sep. 14, 2009

(51) Int. Cl.
*H03F 3/45* (2006.01)

(52) U.S. Cl. .................... 330/69; 330/258; 330/147; 330/124 R

(58) Field of Classification Search ............ 330/69, 330/258, 124 R, 147; 600/509
See application file for complete search history.

(56) References Cited

U.S. PATENT DOCUMENTS

| | | | | |
|---|---|---|---|---|
| 4,928,692 A | * | 5/1990 | Goodman et al. | ............ 600/324 |
| 5,146,179 A | * | 9/1992 | Carley et al. | ................ 330/253 |
| 5,417,221 A | * | 5/1995 | Sickler | ...................... 600/509 |
| 5,999,597 A | * | 12/1999 | Brown | ...................... 379/93.05 |
| 6,493,576 B1 | * | 12/2002 | Dankwart-Eder | ........... 600/544 |
| 6,972,623 B2 | * | 12/2005 | Chang et al. | ................ 330/253 |

* cited by examiner

*Primary Examiner*—Patricia Nguyen
(74) *Attorney, Agent, or Firm*—Garcia-Zamor IP Law; Ruy M. Garcia-Zamor

(57) ABSTRACT

This invention relates to a fully differential non-inverting parallel amplifier for detecting biology electrical signal, including input buffer circuits, differential filter circuits, data selector, non-inverting parallel amplifying circuits and analog-digital circuits. The biology electrical signal, first impeded and converted by the input buffer circuits, and then low-pass filtered by the differential filter circuits, shall be amplified with its common mode signal rejected by passing through the data selector and non-inverting parallel amplifier circuits. At last, the amplified biology electrical signal is output by analog to digital conversion in the analog-digital circuits after its noises beyond signal high frequency band are filtered by anti-aliasing filter net. This invention, with low noise and high common mode rejection ratio, stable baseline, large signal input dynamic range, is reliable and not easy to be saturated. Furthermore, it can support mature PACE Detecting with a low cost. It is notable in social and economical benefits for its simple electrical circuits and easy use in any biology electrical testing equipments and controlling system.

6 Claims, 1 Drawing Sheet

FULLY DIFFERENTIAL NON-INVERTED PARALLEL AMPLIFIER FOR DETECTING BIOLOGY ELECTRICAL SIGNAL

TECHNICAL FIELD

The invention relates to a device for detecting biology electrical signal, in particular, a fully differential non-inverting parallel amplifier for detecting biology electrical signal.

BACKGROUND ART

It is well known that all biology electrical signal testing are carried out in a circumstance of strong background interference or existing patient pillaring voltage. In this connection, an amplifier has to be used because of strong interference (power-frequency interference especially). Unfortunately, biology electrical signals are usually weak and have to be amplified hundreds times or more. In addition, polarizing voltage is generated when electrode touches skin, which makes the first gain of amplifier weak. Then a second amplifying has to be carried out after isolating polarizing voltage by resistance-capacitance circuits. However, because of time constant circuits, the capacitors shall be charged when patients' polarizing voltage is high which makes the first output saturated. As if the patient is in a stable state (the maximum polarizing voltage reaches a low normal value), then it needs a very long time to release the charge of stop capacitor, which makes it is impossible to gather ECG signal during this period. So the communication device is slow in generating signals and its base line is easy to be shifted but slow to be recovered. To sum up, the traditional AC magnitude has the following defects such as small signal dynamic range, complex circuits, big noise, saturated amplifier, slow baseline recovery (baseline shifting), pacemaker (PACE) pulse testing, weak noise immune, losing signal direct current or AC signals similar to direct current signals and so on.

To solve the above stated problems, direct current amplifier circuits with instrumentation amplifier is popularly applied, however, the traditional direct current amplifier still have the following defects;

Firstly, the circuits is still complicated and with many amplifying steps, which is not good for controlling system noises and weak in restraining common mode interference. At the same time, all the signals from instrumentation amplifier are all single-ended signals, which makes it is impossible to eliminate the common mode interference caused by signals joined incidentally.

Secondly, it is costly. Almost all the instrumentation amplifier is with a high price. Even if the instrumentation amplifier put up by trinary operational amplifier is adopted, on the one hand the cost is still much higher than the non-inverting parallel amplifier; on the other hand its common mode rejection ratio is hard to be enhanced because of low precision of resistance matching. Usually, 60 dB is already very good.

In conclusion, to adopt traditional direct current amplifier circuits is hard to solve the problems of high cost and low common mode rejection ratio.

CONTENTS OF THE INVENTION

Aiming at the shortcomings above in existing technology, this invention is to provide a fully differential non-inverting parallel amplifier for detecting biology electrical signals with low cost and high efficiency. It simplified the design of biology electrical front-end circuits greatly and enables high efficiency and low cost possible.

For achieving the objective above, this invention adopts the following technical solution:

A fully differential non-inverting parallel amplifier for detecting biology electrical signal, characterized in comprising an input buffer circuits, a differential filter circuits, a data selector, an non-inverting parallel amplifying circuits and an analog-digital circuits; wherein the biology electrical signal, first impeded and converted by the input buffer circuits, and then low-pass filtered by the differential filter circuits, shall be amplified with its common mode signal rejected by passing through the data selector and non-inverting parallel amplifier circuits; at last, the amplified biology electrical signal be output by analog to digital conversion in the analog-digital circuits after its noises beyond signal high frequency band are filtered by anti-aliasing filter net.

The foresaid input buffer has nine circuits U1~U9; each circuits is comprised by one low-noise single operational amplifier which is connected like voltage follower, and its non-inverting input is connected with the circuits current limiting resistance while the inverting input is connected with output end and the input end of differential filtering circuits.

The differential filtering circuits has eight circuits; each circuits has first order differential low pass filter comprised by two resistances and one capacitor; one end of the resistance is connected with the output end of buffer circuits while the other is connected with capacitor filter and data selector input as well, and both ends of the capacitor filter are connected with resistance filter separately.

The foresaid data selector is an analog switch of analog-digital converter internal integration with high resolution which can be equipped as one choosing from eight differential input and output, and 8 differential input ends shall be connected with conductor I and II and the outputs of differential filter V1-V6.

The foresaid differential non-inverting parallel amplifying circuits is one circuits; wherein the circuits mainly includes double operational amplifier U10, U11, resistance R19-R23 and capacitor C9; The non-inverting end of U10 is connected with the normal phase output MUXP of data selector; the non-inverting end of U11 is connected with the negative output MUXN of U12; the inverting end of U10 and U11 is connected with resistance R19: the inverting end of U10 and U11 are connected with output of U10 and U11 through R20 and R21 separately; the output of U10 and U11 are connected with one end of R22 and R23 in filtering net; the other end of R22 and R23 are connected with capacitor filter C9 and the positive input IN+ and negative input IN− of analog-digital converter at the same time.

The IN+ and IN− of analog-digital converter are connected with R22 and R23 separately, and the digital signal output is connected with microprocessor through SPI or LVDS.

By adopting the above foresaid technical proposals, this invention, with low noise and high common mode rejection ratio, stable baseline, large signal input dynamic range, is reliable and not easy to be saturated. It can support mature PACE Detecting. In addition, its cost is much lower than the classical direct current amplifier adopting integrating circuits. At the same time, its simple circuits and high integration is easy for card miniaturization. This product, easily to be produced and sold, can be widely used in all kinds of biology electrical testing such as ECG, mental EEG and myoelectricity and so on. It is notable in social and economical benefit.

MODE OF CARRYING OUT THE INVENTION

Figure 1:
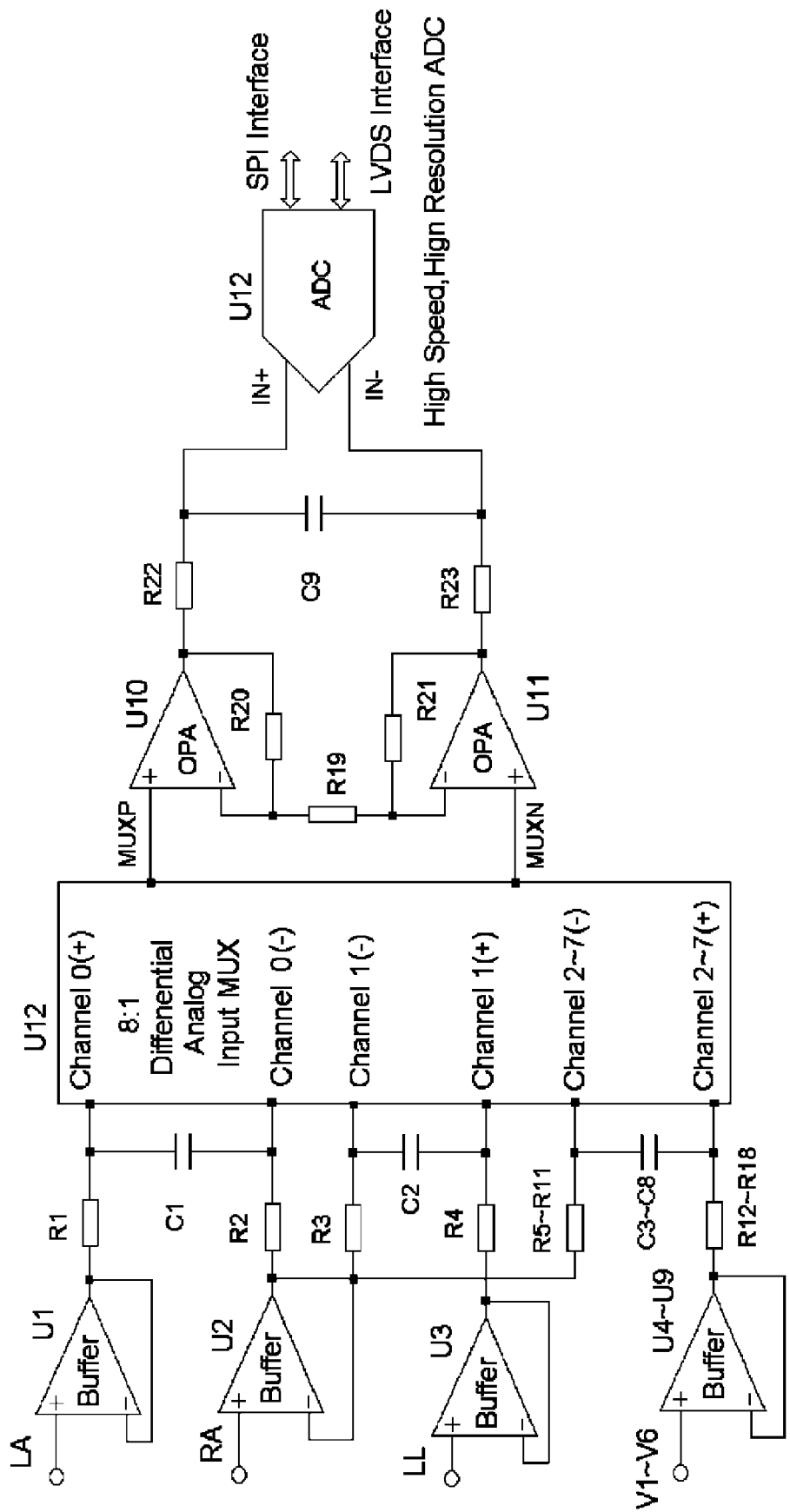
FIG. 1 is the electric schematic diagram of this invention.

Further explanation to the invention is stated below combining with the attached figures:

Referring to FIG. 1, this fully differential non-inverting parallel amplifier for detecting biology electrical signal, including input buffer circuits, differential RC circuits, channel selector, non-inverting parallel amplifying circuits and analog-digital circuits. The biology electrical signal, first impeded and converted by the input buffer circuits, and then low-pass filtered by the differential filter circuits, shall be amplified with its common mode signal rejected by passing through the data selector and non-inverting parallel amplifier circuits. At last, the amplified biology electrical signal is output by analog to digital conversion in the analog-digital circuits after its noises beyond signal high frequency band are filtered by anti-aliasing filter net.

The input buffer has nine circuits U1-U9. Each circuits is comprised by gas discharge tube, current limiting resistance, capacitor filter, coupling capacitor and two-diode clamp, in which RA is shared together. The other 8 buffers shall minus RA separately. This input buffer circuits is to provide signals sources of low output impedance for the backward stage circuits.

There are 8 circuits for fully differential filter circuits, each of which are comprised by two resistances and one capacitor. By adopting fully differential filter circuits, the filter effect is guaranteed and the common mode rejection ratio won't be lowered down by the discreteness of device parameter.

The channel selector, comprised by high resolution ADC integration, can be equipped with one choosing from eight differential analog switches.

The non-inverting parallel differential amplifier is mainly comprised by double operational amplifier U10, U11, resistance R19-R23 and capacitor C9. The non-inverting input of U10 is connected to the normal phase output MUXP of data selector U12. The non-inverting end of U11 is connected with the negative output MUXN of U12. The inverting end of U10 and U11 is connected with resistance R19. The inverting end of U10 and U11 are connected with output of U10 and U11 through R20 and R21 separately. The output of U10 and U11 are connected with one end of R22 and R23 in filtering net. The other end of R22 and 823 are connected with capacitor filter C9 and the positive input IN+ and negative input IN− of analog-digital converter at the same time. Known from relative instrumentation amplifier theory, the common mode rejection ratio of the first non-inverting differential amplifier circuits comprised by U10 and U11 is only relevant to the CMRR coherence of U10 and U11, but not to the precision of R19-R23 or the CMRR specification of U10 and U11. This is because the first circuits is non-inverting parallel structure which enables R20 and R21 to be symmetrical and balanced easily. This structure is convenient to eliminate the unmatched influence of resistances, no it is no need to discuss the common mode rejection ability of first circuits external resistance but only the common mode rejection ability of calculation amplifier itself. Actually, no common mode current of first output U1, U2 shall be generated in the loop. The differential voltage on resistance R19 decides all the working current of the whole circuits, but the common mode voltage on this potential device has no influence to this current. No matter how much the value of resistance R19, R20 and R21 is, the results won't be changed. So the circuits common mode rejection ratio has nothing to do with whether it is matching to its outer loop resistance. In addition, the parallel circuits can make use of the principles of symmetry, maladjustment and complement, which counteracts the common mode tolerance voltage to obtain low excursion and high stability. In addition, the different-mode signal can be adjusted easily which makes application convenient.

Both U10 and U11 adopt double operational amplifier. Because they are in the same silicon chip with a high coherence, CMRR value for the non-inverting parallel differential amplifier can be kept high. This is the only circuits providing analog gain which has the following functions: to provide common mode rejection ratio and analog gain; to provide amplifying level of the high input impedance; to lower down the signal loses caused by on-resistance of analog switch; to be double as ADC driver and anti-aliasing filtering.

Analog-digital circuits includes high resolution ADC of differential input and integration one choosing from eight differential analog switches. This ADC foresaid requires high common mode rejection ratio, which works as the third operational amplifier of instrumentation amplifier namely single-ended input operational amplifier and also the final device to restrain common mode signal. It is can be said that keystone of this invention is to get an instrumentation amplifier by combining differential non-inverting parallel circuits and ADC. It omits the instrumentation amplifier chip in the classical direct current amplifier but realizes the same function, which achieved the aim of both high performance and low cost.

The computation formula for the common mode rejection ratio of the whole non-inverting parallel differential amplifier circuits including ADC is as the following:

$$CMRR = \frac{AD_1 * CMRR_{12} * CMRR_3}{AD_1 * CMRR_3 + CMRR_{12}} \quad \text{(Formula 1)}$$

In this formula, CMRR is the common mode rejection ratio for the whole circuits, $AD_1$ is the first differential gain of non-inverting parallel amplifier circuits, $CMRR_{12}$ is the first common mode rejection ratio and $CMRR_3$ is the common mode rejection ratio of ADC. In addition, $CMRR_{12}$ is decided by the common mode rejection ratio of U10 and U11 as the following:

$$CMRR_{12} = \frac{CMRR_1 * CMRR_2}{CMRR_1 + CMRR_2} \quad \text{(Formula 2)}$$

In the formula 2, CMRR1 and CMR2 are the common mode rejection ratio of U10 and U11 operational amplifiers separately. By adopting integration double operational amplifier, a close parameter is guaranteed by the same technique. Generally, the difference between $CMRR_1$ and $CMRR_2$ can be only 0.5 dB, therefore the $CMRR_{12}$ decided by formula 2 can be above 160 dB. In this connection, formula 1 can be simplified as:

$$CMRR = AD_1 * CMRR_3 \quad \text{(Formula 3)}$$

The above formula is an expression to common mode rejection ratio of the whole structure of non-inverting differential amplifier circuits, in which $AD_1$ is the first differential gain of non-inverting differential amplifier and CMRR3 is the common mode rejection ratio of high resolution ADC. This foresaid expression is the same as instrumentation amplifier common mode rejection ratio comprehension formed by classical trinary operational amplifier. Known from formula 3, instrumentation amplifier gain should be arranged at the first grade to obtain a higher CMRR. It is can be said to enhance AD1 and increase the common mode rejection ratio CMRR3 of the trinary operational amplifier including peripheral resistance. Generally speaking, it is difficult to make resistance precision to be 10E-4 because it is demanding to make the CMRR3 matching to the trinary operational amplifier peripheral resistance of classical instrumentation amplifier as much as possible. Usually, the CMRR3 can only be 80 dB. When the overall gain is 2 (the first instrumentation gain is 2 and second differential gain is usually 1 in this example), the CMRR of classical trinary operational amplifier can only be 86 dB. Here only refers to integration instrumentation amplifier with a good resistance matching. If the instrumentation amplifier is put up by discrete trinary operational amplifier and resistance, the resistance precision can only be 10E-3 and CMRR is only around 66 dB at the maximum.

By adopting high resolution ADC, this common mode rejection ratio usually can be 50/60 HZ@90 Db. Because it is the common mode rejection ratio provided by ADC, the adverse effect of matching precision of usual instrumentation amplifier circuits. In this non-inverting differential amplifier circuits, as is the gain of non-inverting parallel level can be 2, then the CMRR of the whole circuits can be 96 dB which means that the key indicators CMRR is not only much higher than that of instrumentation amplifier put up by discrete trinary operational amplifiers (above 30 dB) but also superior to the classical integration instrumentation amplifier. In addition, its cost is much lower than the circuits adopting integration instrumentation amplifier but with an excellent performance. It is obviously in advantage in multichannel cardiogram electroencephalogram application.

What is claimed is:

1. A fully differential non-inverting parallel amplifier for detecting biology electrical signal, characterized in that it includes input buffer circuits, differential filter circuits, data selector, non-inverting parallel amplifying circuits and analog-digital circuits; wherein the biology electrical signal, first impeded and converted by the input buffer circuits, and then low-pass filtered by the differential filter circuits, shall be amplified with its common mode signal rejected by passing through the data selector and non-inverting parallel amplifier circuits; then, the amplified biology electrical signal is output by analog to digital conversion in the analog-digital circuits after its noises beyond signal high frequency band are filtered by anti-aliasing filter net.

2. A fully differential non-inverting parallel amplifier for detecting biology electrical signal as set forth in claim 1, characterized in that the foresaid input buffer has nine circuits U1~U9; each circuits is comprised by one low-noise single operational amplifier which is connected like voltage follower; and its non-inverting input is connected with the circuits current limiting resistance while the inverting input is connected with output end and the input end of differential filtering circuits.

3. A fully differential non-inverting parallel amplifier for detecting biology electrical signal as set forth in claim 1, characterized in that the differential filtering circuits has eight circuits; each circuits has first order differential low pass filter comprised by two resistances and one capacitor; one end of the resistance is connected with the output end of buffer circuits while the other is connected with capacitor filter and data selector input as well; and both ends of the capacitor filter are connected with resistance filter separately.

4. A fully differential non-inverting parallel amplifier for detecting biology electrical signal as set forth in claim 1, characterized in that the foresaid data selector is an analog switch of analog-digital converter internal integration with high resolution which can be equipped as one choosing from eight differential input and output, and 8 differential input ends shall be connected with conductor I and II and the outputs of differential filter V1-V6.

5. A fully differential non-inverting parallel amplifier for detecting biology electrical signal as set forth in claim 1, characterized in that the foresaid differential non-inverting parallel amplifying circuits is one circuits; the circuits mainly includes double operational amplifier U10, U11, resistance R19-R23 and capacitor C9; wherein the non-inverting end of U10 is connected with the normal phase output MUXP of U12; the non-inverting end of U11 is connected with the negative output MUXN of U12; the inverting end of U10 and U11 is connected with resistance R19; the inverting end of U10 and U11 are connected with output of U10 and U11 through R20 and R21 separately; the output of U10 and U11 are connected with one end of R22 and R23 in filtering net, while the other end of R22 and R23 are connected with capacitor filter C9 and the positive input IN+ and negative input IN− of analog-digital converter at the same time.

6. A fully differential non-inverting parallel amplifier for detecting biology electrical signal as set forth in claim 5, characterized in that the IN+ and IN− of analog-digital converter are connected with R22 and R23 separately, and the digital signal output is connected with microprocessor through SPI or LVDS.

* * * * *